(12) United States Patent
Cecchi

(10) Patent No.: US 7,157,270 B2
(45) Date of Patent: Jan. 2, 2007

(54) LIGHTWEIGHT CHAMBER HAVING VARIABLE CONFIGURATIONS AND A METHOD FOR MAKING SUCH

(75) Inventor: Michael D. Cecchi, Madison, CT (US)

(73) Assignee: genX international inc., Guilford, CT (US)

( * ) Notice: Subject to any disclaimer, the term of this patent is extended or adjusted under 35 U.S.C. 154(b) by 529 days.

(21) Appl. No.: 10/131,632

(22) Filed: Apr. 24, 2002

(65) Prior Publication Data

US 2003/0203479 A1    Oct. 30, 2003

(51) Int. Cl.
*C12M 1/00* (2006.01)
(52) U.S. Cl. .............................. 435/289.1; 435/303.1; 435/809; 312/209
(58) Field of Classification Search ............ 435/286.6, 435/303.1, 809; 422/104; 312/31, 107, 312/108, 111, 236, 257.1, 263, 264, 265.5, 312/265.6, 31.02, 209, 409, 351; 220/4.01, 220/4.28, 4.31, 4.32, 500, 501, 553, 592.28; 600/22; 219/400; 34/219, 225; 52/309.1, 52/2.11; 211/135, 90.04, 134, 188
See application file for complete search history.

(56) References Cited

U.S. PATENT DOCUMENTS

| | | | | |
|---|---|---|---|---|
| 101,244 | A | * 3/1870 | Estabrooks | ............. 220/573.4 |
| 3,743,130 | A | * 7/1973 | Jorgensen | ..................... 383/38 |
| 5,505,329 | A | * 4/1996 | Kauffman | ................ 220/62.11 |
| 5,792,427 | A | 8/1998 | Hugh et al. | ................. 422/109 |
| 5,958,763 | A | * 9/1999 | Goffe | ...................... 435/303.1 |
| 6,013,119 | A | 1/2000 | Cecchi et al. | .............. 55/385.2 |
| 6,117,687 | A | 9/2000 | Hugh | ......................... 436/183 |
| 6,200,362 | B1 | 3/2001 | Cecchi et al. | ................. 55/486 |
| 6,225,110 | B1 | 5/2001 | Cecchi et al. | ............ 435/303.1 |
| 2002/0009803 | A1 | 1/2002 | Vajta | ......................... 435/325 |
| 2003/0138942 | A1 | 7/2003 | Cecchi et al. | ............ 435/288.7 |

FOREIGN PATENT DOCUMENTS

| | | | |
|---|---|---|---|
| EP | 0290923 | * | 5/1988 |
| EP | 290923 A2 | * | 11/1998 |
| JP | 11211342 | * | 8/1999 |
| WO | WO 88/07574 | | 10/1988 |

OTHER PUBLICATIONS

European Search Report dated Jan. 2, 2004 (3 pp.) for corresponding application No. 03252533.9-2404.

* cited by examiner

*Primary Examiner*—David Redding
(74) *Attorney, Agent, or Firm*—George N. Chaclas, Esq.; Edwards Angell Palmer & Dodge, LLP

(57) ABSTRACT

An anabolic chamber constructed of a plastic with additives to create desirable characteristics such as resistance to corrosion and bacteria growth. The anabolic chamber has a double-wall structure with internal support ribs for creating a water jacket for facilitating maintaining temperature control within the chamber. Features such as handles, mounting blocks and surface detail are created integral to the anabolic chamber.

24 Claims, 3 Drawing Sheets

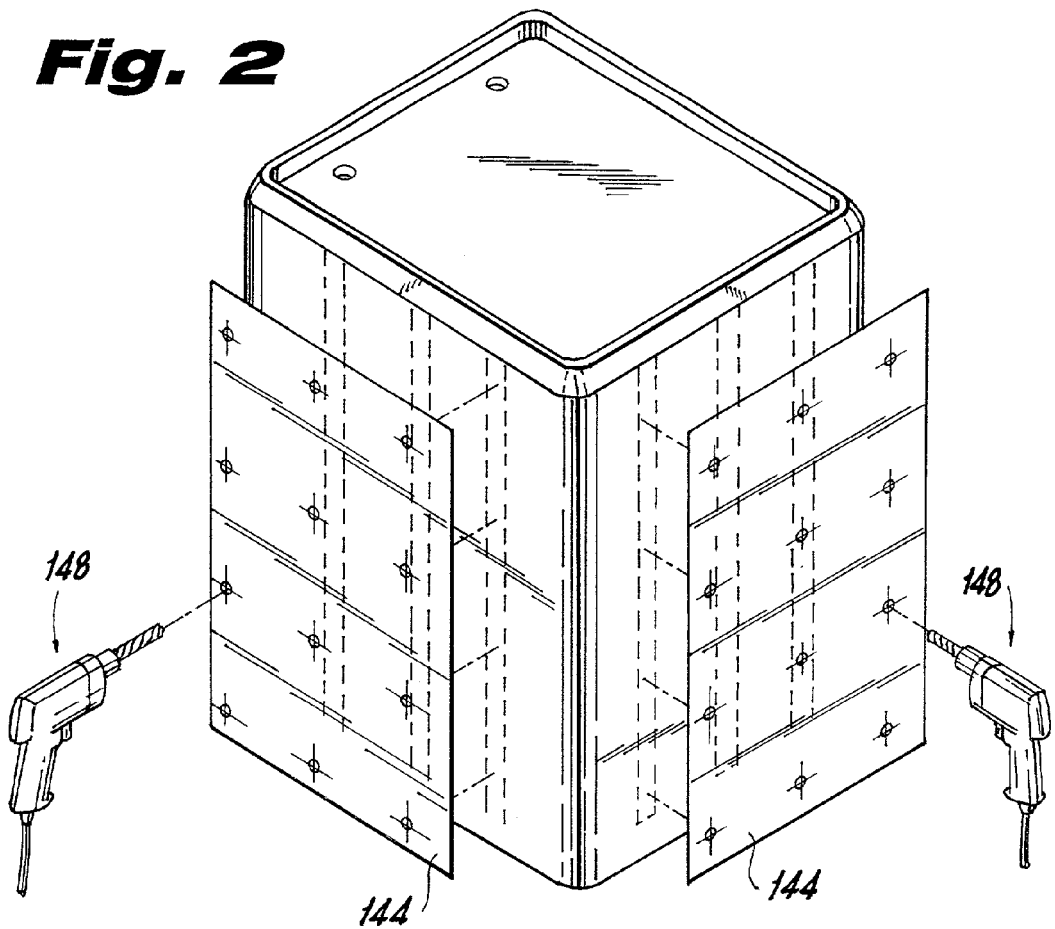
Fig. 2
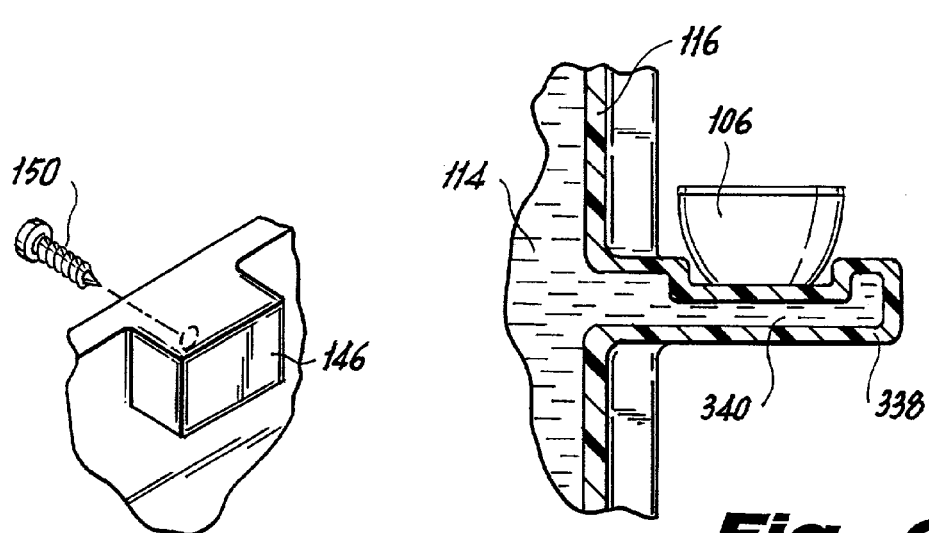
Fig. 3
Fig. 6

LIGHTWEIGHT CHAMBER HAVING VARIABLE CONFIGURATIONS AND A METHOD FOR MAKING SUCH

BACKGROUND OF THE INVENTION

1. Field of the Invention

The subject invention relates to systems for culturing biological specimens, and more particularly, to an anabolic chamber having variable access ports, variable mounting features, improved cleanliness and decreased weight relative to prior art systems.

2. Background of the Related Art

Incubators are used to maintain environment sensitive specimens such as human embryos under desirable conditions. The use of stainless steel housings for incubators is well known in the art. Generally, the stainless steel housing defines an interior chamber surrounded by a water jacket for maintaining temperature control. Alternatively, direct heat may be applied to the exterior of the chamber to maintain temperature control. Shelves within the interior chamber support specimens. Techniques have been also developed to maintain a constant, as well as filter the air, within the interior chamber.

Stainless steel enclosures are both heavy and difficult to fabricate. The welded corners and joints need to be polished to provide a smooth surface which can be cleaned. The welding and polishing is an expensive and difficult process. If the polishing and cleaning is poorly performed, molds, spores and other bacteria can grow thereon. Further, the interior chamber defines right angle corners which provide an area for undesirable contamination to collect, which can be difficult to successfully clean by technicians. Additionally, monitoring and other devices such as video cameras, acoustic sensors, air filtration units and the like require costly addition of mounting fixtures within the interior chamber. Further, connection of internal devices to external apparatus is difficult particularly when a water jacket is employed. With traditional stainless steel chambers, adding additional features after production and creating a pass-through to the interior chamber is impossible or at least limited.

Several systems have been developed to provide access to and control of the conditions of the interior of an incubator. Some examples are illustrated in U.S. Pat. No. 6,013,119 to Cecchi et al., U.S. Pat. No. 5,792,427 to Hugh et al. and U.S. Pat. No. 6,225,110 to Cecchi et al., each of which is incorporated herein by reference. For example, one parameter which is desirable to control within the incubator is the cleanliness of the air. Generally, an air circulation system includes a blower for forcing the air within the interior through a filtering mechanism and back into the interior. Sophisticated feedback mechanisms may be employed to maintain humidity and temperature within prescribed ranges.

As appropriate for the specific application, a plurality of fixtures or support structures may exist within the interior. For example, at great expense and difficulty, conventional stainless steel incubators have anchors spot welded for securing shelving and other user selectable fixtures. Often, when the water jacket is filled, the walls of the incubator bow and the fixtures either fit improperly or the anchors cease to function altogether. Shelving units may be configured to enhance air flow and access to specimens as taught in U.S. patent application Ser. No. 09/693,595 to Cecchi et al. and U.S. patent application Ser. No. 10/053,944 to Cecchi et al., each of which is incorporated herein by reference.

In a laboratory environment, it is often desirable to relocate or reconfigure an incubator. The excessive weight of stainless steel construction is an impediment to handling and stacking. Further, the ability to retrofit a stainless steel incubator is cost prohibitive, if existent at all. In view of this, some technology has recognized the need for varying the configuration of the incubator externally in order to provide flexibility in laboratory configuration. In particular, U.S. Pat. No. 6,117,687 to Hugh, incorporated herein by reference, discloses an incubator door which can be reversed in the field by way of a reversible hinge mounting assembly. However, such retrofit techniques have not proven to be cost effective and provide only limited variation of configuration. Further, no latent features are present which would allow reconfiguration of the incubator. Latent features allow capabilities, such as shelf mounts and access ports, to be present in the incubator and utilized, after production, as desired by the specific application.

There is a need, therefore, for an improved incubator which permits easy movement and/or reconfiguration, assures adequate cleanliness and maintains desirable conditions for the specimens.

SUMMARY OF THE INVENTION

An incubator for culturing specimens having a body defining an interior chamber and an opening for accessing the interior chamber. The body has integral features for providing mounts and access. A door selectively seals the opening and a control module secured to the body maintains conditions within the interior chamber. The integral features provide flexibility in modifying the configuration of the incubator depending upon the particular desired features.

The incubator is preferably made of a light weight, durable material. As a result, the incubator can be moved and cleaned easily. Stacking of the incubators is facilitated not only by the shape of the top and bottom surfaces but by the ability to reconfigure for varying configurations.

These and other unique features of the system disclosed herein will become more readily apparent from the following description, the accompanying drawings and the appended claims.

BRIEF DESCRIPTION OF THE DRAWINGS

So that those having ordinary skill in the art to which the disclosed system appertains will more readily understand how to make and use the same, reference may be had to the drawings wherein:

FIG. 2 is a perspective view of the incubator of FIG. 1 with templates for locating latent features;

FIG. 3 is an enlarged localized view of a latent mounting block as shown in FIG. 1;

FIG. 6 is a partial cross-sectional view of another shelf constructed in accordance.

DETAILED DESCRIPTION OF THE PREFERRED EMBODIMENT

Figure 1:
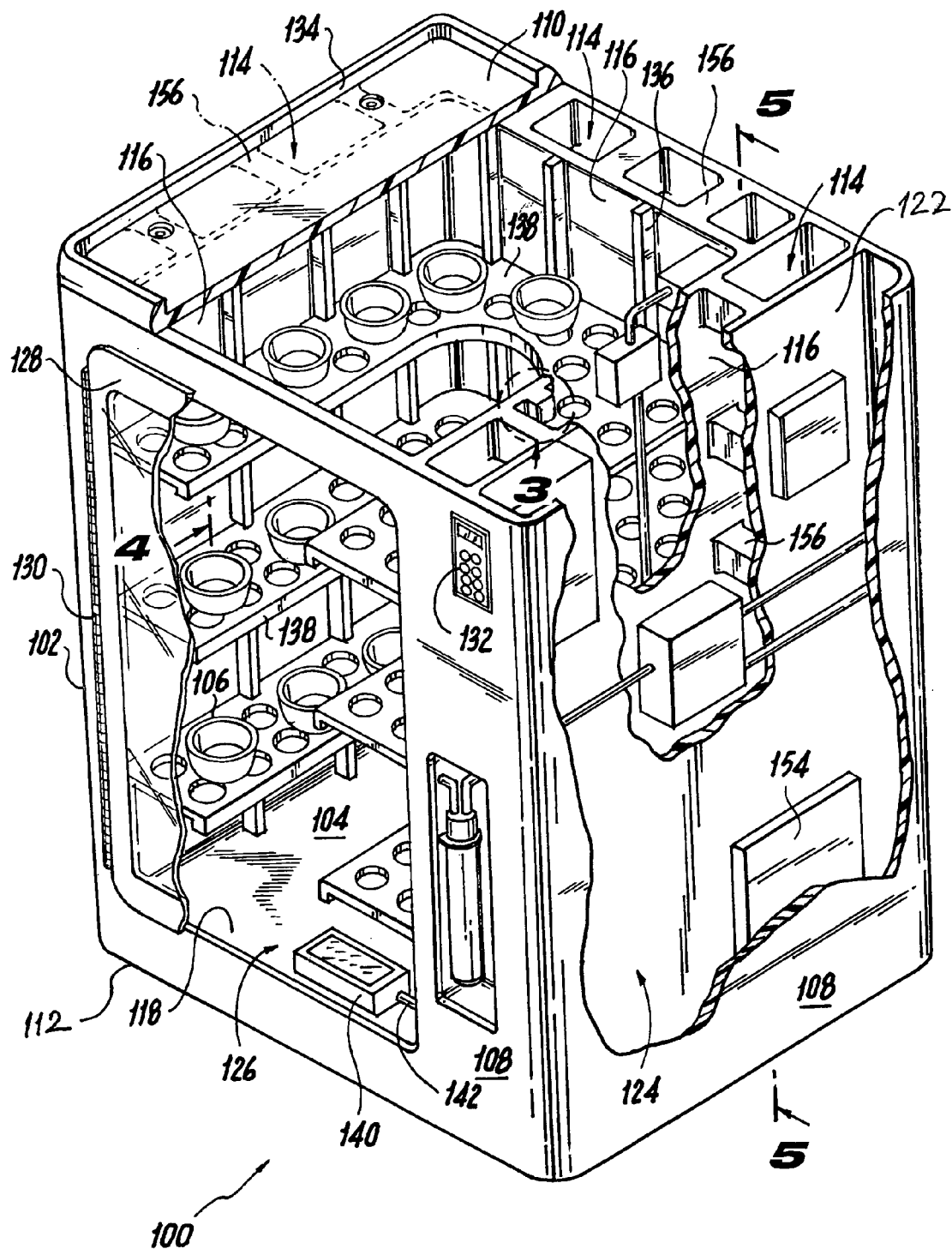
FIG. 1 is a perspective view of an incubator for containing specimens constructed in accordance with a preferred embodiment of the subject disclosure, with the outer wall broken away so as to illustrate the interior of the incubator.

The present invention overcomes many of the prior art problems associated with conventional incubators. The advantages, and other features of the system disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Referring to FIG. 1, an anabolic chamber, designated generally by reference numeral 100, includes a double-walled body portion 102 for defining an interior 104 which maintains specimens 106 in an environmentally controlled clean environment. It is envisioned that the specimens are human embryo cultures and other like environmentally sensitive objects. The substantially box-shaped body portion 102 includes four outer walls 108, an upper ceiling 110 and a base floor (not shown). A jacket space 114 is defined between three inner walls 116 and the corresponding outer walls 108. An inner floor 118 allows the jacket space 114 to continue about the base floor 112 of the body portion 102. In another embodiment, an inner ceiling (not shown) allows the jacket space to continue about the upper ceiling of the body portion. An intermediate wall 122 extends between the inner and outer walls on a side of the incubator 100 for defining a chase area 124. The chase area 124 stores a portion of the supporting components necessary for maintaining the clean environment within the anabolic chamber 100.

An opening 126 in the front outer wall provides access to the interior 104 within the body portion. A door 128 is secured to the front outer wall by a hinge 130 and selectively seals the opening. Adjacent to the opening, a keypad 132 integral with the outer wall receives user input. The upper ceiling includes a perimeter ridge 134 and the base floor includes a recess (not shown). When multiple anabolic chambers 100 are stacked, the recess of the base floor receives the ridge 134 to secure the anabolic chambers 100 in place.

In the preferred embodiment, the anabolic chamber 100 is of a lightweight monolithic construction having a plurality of fixtures such as mounting brackets 136 within the interior 104. As shown, the mounting brackets 136 support a plurality of shelves 138 for holding specimens 106. The anabolic chamber 100 also has a plurality of latent features. The latent features would be utilized as required for the specific application. For example, without limitation, the latent features may provide air, water and probe ports, as well as solid portions for mounting fixtures thereto.

Preferably, the body portion of the anabolic chamber 100 is constructed using a rotational molding process. Rotational molding is a manufacturing option that allows for a monolithic design having integral latent features. Generally, the rotational molding process places a mold in a molding machine that has a loading, heating, and cooling area. Pre-measured plastic resin is loaded into each mold, and then the molds are moved into an oven where they are slowly rotated on both the vertical and horizontal axis. The melting resin sticks to the hot mold and coats every surface evenly. The mold continues to rotate during the cooling cycle so the parts retain an even wall thickness. Upon cooling, the parts are released from the mold. The rotational speed, heating and cooling times are all controlled throughout the process. As a result, what would be required from a plurality of pieces of stainless steel can be molded as one part, eliminating expensive fabrication costs. The process also has a number of inherent design strengths, such as consistent wall thickness and strong outside corners that are virtually stress free.

Rotational molding also allows selection of variable material, including materials that meet FDA requirements. It will be appreciated by those of ordinary skill in the pertinent art that polymer resin, plastic resin, composites, the like, and combinations thereof can be used as the material for the body portion. Further, additives can be selected to help make the resulting parts weather resistant, flame retardant, anti-microbial, mildew retardant, and static free. Inserts, threads, handles, minor undercuts, fine surface detail such as snap-fit slots for engaging objects, and the like can be incorporated into the mold rather than as a later addition. Preferably, the corners of the interior 104 are coved to allow for easy cleaning. Temporary modifications to an existing mold for a particular application allow further product customization. Thus, all of the necessary features are formed integral to the body portion and the resulting smoother surface of formed plastic is easier to clean.

Still referring to FIG. 1, the jacket space is filled with water for maintaining temperature control within the anabolic chamber 100. Structural ribs within the body portion prevent distortion of the walls of the anabolic chamber 100 when filled. As a result of the structural support provided by the ribs, the walls of the anabolic chamber 100 are relatively thinner which in turn increases the storage capacity over a traditional sized incubator. Stacking the anabolic chambers 100 conserves additional floor space within the laboratory.

The chase area 124 of the anabolic chamber stores additional instrumentation. Inputs from the key pad are received by a control module within the chase area to facilitate controlling environmental parameters with the interior 104. Additionally, the control module receives inputs from sensors and the like within the interior 104 and displays the results on a readout panel portion of the key pad. The readout panel portion also provides indication of the current settings for the interior 104. A drive, associated with the control module, receives a medium suitable for recording data related to the conditions within the interior 104. The drive may receive CD ROMs, VHS tapes, diskettes and the like and the data stored thereon may be video, acoustic, temperature, humidity, airflow and the like data as is known to one of ordinary skill in the pertinent art. It is well within the skill of those of ordinary skill in the pertinent art to locate the chase area in another location as would be desired and apparent based upon review of the subject disclosure.

Shelves 138 are secured within the interior 104 for supporting specimens. It is envisioned that the shelf configuration enhances air circulation within the interior 104, and enables unimpeded access to the specimens 106 that are supported thereon. Preferably, the shelves allow a technician to reach every specimen without interfering with other specimens within the anabolic chamber 100. A humidifying pan 140 is filled with distilled water to humidify the interior 104. The humidifying pan 140 receives a conduit 142 such that recirculated air passes through the humidifying pan via the conduit 142.

Referring now to FIG. 2, latent features allow reconfiguration of the anabolic chamber 100 in the laboratory as desired by the user. For example, upon installation and use, a technician may desire an additional port for coupling air filtration power and sensor units to the interior 104. With conventional stainless steel incubators, opening an additional access port after manufacture is impractical. However, a latent feature of the anabolic chamber 100 may be easily opened without affecting the anabolic chamber 100 performance. It is envisioned that the latent features are present not only in between the walls and floors, but the ceiling would be of a suitable thickness for supporting modification as well.

In one embodiment, the latent features are located using a template 144. In another embodiment, predetermined indicator marks are molded integral to the body portion 102. In still other embodiments, indicator marks are cut into or silk-screened onto the body portion 102. The template 144 is aligned with the outside corners of the anabolic chamber 100 to indicate the position of the latent features. Alternatively, the anabolic chamber 100 may be provided with measurements for locating the latent features. It is envisioned that the latent features may be located on any desirable location of the anabolic chamber 100.

For another example, the latent feature may be a portion 146 of added thickness as shown in FIG. 3. Using a conventional drill 148, the thick portion 146 can be drilled and tapped to receive a threaded fastener 150. Upon drilling a portion of the mounting block to create a hole, the hole may be tapped to support a threaded fastener 150. A mounting block can secure a desired feature such as a shelf bracket or additional instrumentation and components to the anabolic chamber 100. The thick portion 146 may be located on inner walls, or the outer wall, the upper ceiling, the inner ceiling, the base floor and the inner floor of the body portion. Preferably, the thick portion 146 is formed during the molding process by providing a structure upon which the resin may collect.

Figure 7:
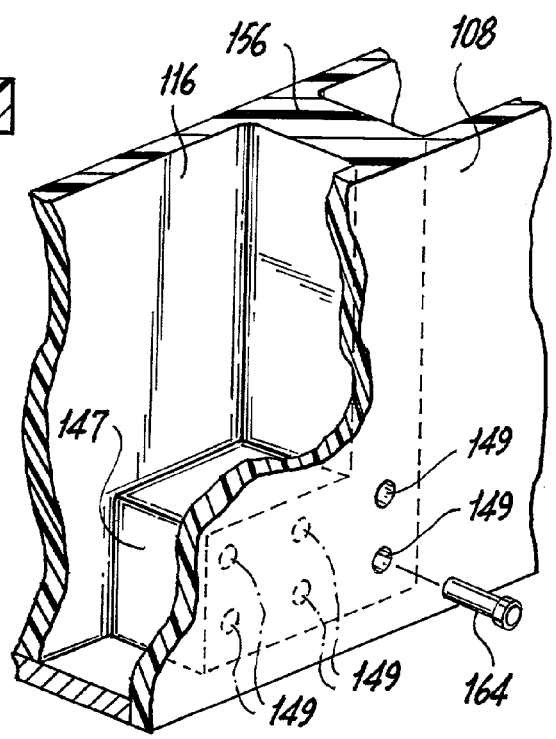
FIG. 7 is an enlarged localized view of another latent mounting block.

Referring to FIG. 7, another preferred mounting portion 147 is illustrated. Portion 147 is a solid bridge between inner wall 116 and outer wall 108. The portion 147 is adjacent to a support rib 156 although it will be appreciated by those skilled in the art that the portion 147 could be located at a plurality of different locations. Portion 147 has a plurality of holes 149 some of which are shown in phantom line. The holes 149 could be used to mount items inside or outside the incubator 100 with a pin 164. Alternatively, the holes 149 could create passthroughs from the outside to the inside of the incubator 100. It will be appreciated by those skilled in the art that considerable variations from that illustrated are possible and that such variations are well within the scope of the subject disclosure. As a result, a simple opening can be created in an inner wall 116, outer wall 108, ceiling, or floor for mounting in conjunction with a screw, bolt, and gasket as is known to those skilled in the art.

Figure 4:
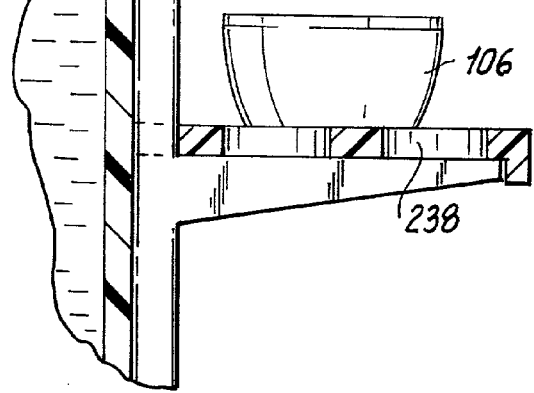
FIG. 4 is a partial cross-sectional view of a shelf taken along line 5—5 of FIG. 1.

Referring to FIG. 4, a shelf 238 is shown supporting a specimen 106 within the interior 104. The shelf 238 is press-fit into a feature integral with the inner wall 116. In another embodiment, a bracket is mounted to the inner wall 116 of the body portion 102 for securely engaging the shelf 238 thereon. The bracket may be mounted by a fastener to the inner wall 116 by preparing a solid portion, structural rib or a combination thereof. Preferably, the preparation consists of drilling and tapping the latent feature. In another embodiment, surface detail such as a channel for a hanging rail is incorporated into the interior surface for securely receiving shelves or additional features by protruding hooks, camming surfaces and the like.

Figure 5:
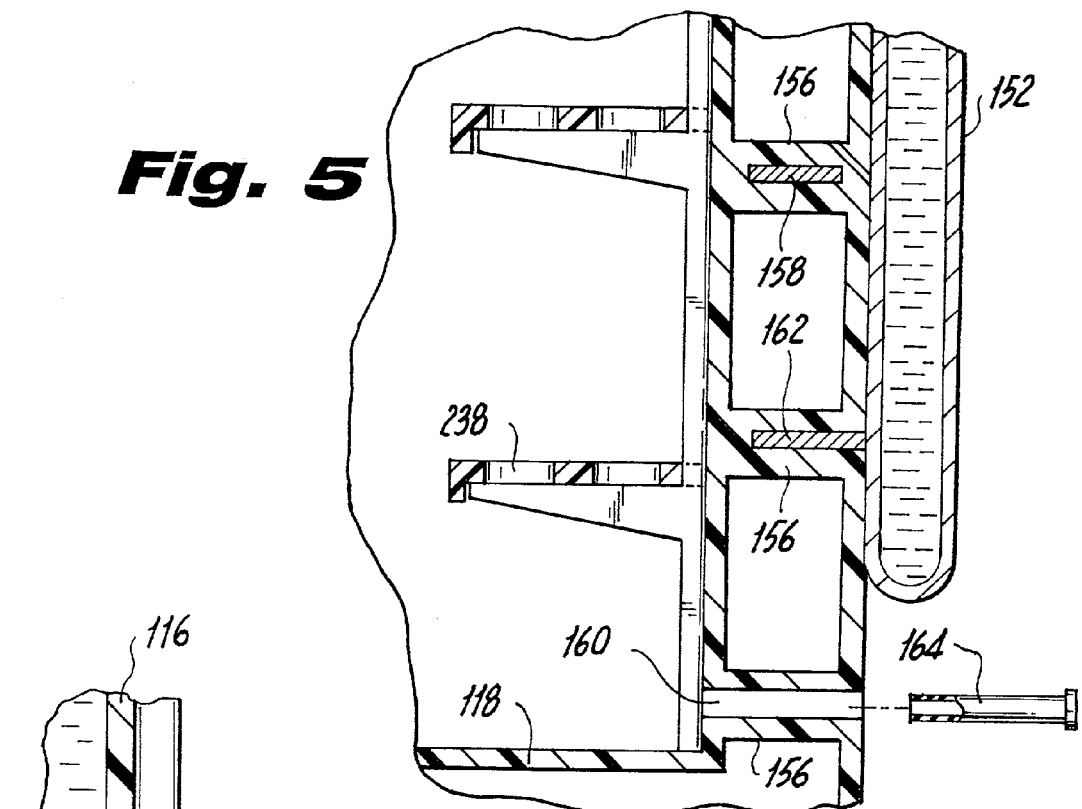
FIG. 5 is a partial cross-sectional view of support ribs taken along line 5—5 of FIG. 1.

Referring now to FIG. 5, one or more elements 152 maintain the temperature of the water within the jacket space 114 and therefore the interior 104. In an embodiment without the jacket space 114, an element 152 more directly maintains the temperature of the interior 104. In the preferred embodiment, the element 152 heats the interior 104 to promote anabolic growth. It is envisioned that the element 152 may heat and/or cool the surface in contact therewith as would be known to one of ordinary skill in the pertinent art.

Also, it is to be appreciated that the remaining description refers to a heating element in the singular for simplicity.

Preferably, the elements 152 are flexible to adhere to the contour of the anabolic chamber 100 and deliver heat precisely and locally over the area to be heated. Preferably, the elements 152 are a fiberglass reinforced silicone rubber element available from Electro-Flex Heat of Bloomfield, Conn. The desirable properties include resistance to temperature extremes, moisture, weathering, radiation, fungus, inertness from chemical attack, high dielectric strength and flexibility. Further advantages are that odd shapes, holes, cutouts, profiled watt densities, and multiple voltages can be accommodated. In a preferred embodiment, the elements 152 are directly bonded to the area to be heated with pressure sensitive adhesive. Alternatively, fasteners such as eyelets, lacing hooks, hook-and-pile straps, spring clips, snaps and the like can be utilized. When an anabolic chamber 100 is reconfigured internally and externally, the element 152 can be temporarily removed or moved to a new location on the anabolic chamber 100. It is also envisioned that thermostats of various types and temperature sensors such as thermistors, thermal-fuse, or thermocouples can be built into the heater and provide feedback to the control module 154 (see FIG. 1). In another preferred embodiment, the element 152 is molded directly over the anabolic chamber 100 to insure an efficient contact area for heat transfer.

Still referring to FIG. 5, support ribs 156 are formed during the molding process to add structure and rigidity to the body portion 102. For example, a mold may contain a pin 158 which collects resin. Upon completion, the resin completely engulfs the pin 158 between adjacent walls to form support therebetween, i.e. the support rib 158. Preferably, support ribs 158 also serve as latent features. If necessary, the element 152 is temporarily peeled away to access the support ribs. Upon locating a desired latent port, a conventional drill and bit is used to reconfigure the anabolic chamber 100, i.e., drill a bore through the rib 156 and pin 158 to form the port. The bore can serve as a pass-through such as disclosed in U.S. Pat. No. 6,225,110 to Cecchi et al. and incorporated herein by reference. The bore can be tapped for engaging a threaded fastener or used temporarily and resealed with plugs. Provided the bore is formed within the structural rib 156, the structural rib 156 still supports the sidewalls without leaking. Alternatively, the support rib 156 may be partially drilled out and used similarly as a mounting block as described with reference to FIG. 3. Consequently, any apparatus or component which can be mounted by screws can be secured to the anabolic chamber 100 at various locations. For example, electrical power boxes, additional shelf brackets, sensor brackets, filter units, cameras, data recorders and the like may be mounted inside or outside the anabolic chamber 100 as would be appreciated by those of ordinary skill in the art based upon review of the subject disclosure.

Alternatively, during the molding process a longer pin 164 may be used to collect resin. Upon removal of the pin 164, a throughbore 160 is created as well as additional support. Additionally, the throughbore 160 may be tapped, plugged and the like. In another location, an intermediate length pin (not shown) may collect resin. Upon removal of the intermediate length pin a void 162 is formed for use as would be known to one skilled in the art upon review of the subject disclosure.

Referring to FIG. 6, in another embodiment, the shelves 338 are integral with the body portion 102 and formed during the rotational molding process. The shelves 338 depend from the inner wall 116 and define a hollow 340 which is in fluid communication with the jacket space 114. Such fluid communication allows more refined temperature control not only of the interior 104 but the actual surface in contact with the specimens 106. It is envisioned that other features may be integral with the body portion 102 of the anabolic chamber 100 as would be appreciated by those skilled in the pertinent art upon review of the subject disclosure.

In another embodiment, the chamber is constructed of plastic resin walls of a suitable thickness to allow creating mounting holes, passthroughs and the like in multiple locations as desired. The desired elements such as shelves, a control module, filter unit, heating element and the like can be secured subsequent to manufacture of the chamber as required for the specific application.

While the invention has been described with respect to preferred embodiments, those skilled in the art will readily appreciate that various changes and/or modifications can be made to the invention without departing from the spirit or scope of the invention as defined by the appended claims.

What is claimed is:

1. An anabolic chamber for culturing specimens comprising:
    a body defining an interior and an opening for accessing the interior, said body having walls; and
    at least one portion of added thickness integrally formed with one of the walls for selectively providing at least one mount;
    a door connected to the body to selectively seal the opening; and
    a control module secured by the mounts and operatively connected to the interior for maintaining conditions within the interior.

2. An anabolic chamber as recited in claim 1, wherein the portion is a plurality of shelf supports for supporting a plurality of shelves within the interior.

3. An anabolic chamber as recited in claim 1, wherein the portion is a plurality of solid portions for securely engaging the shelves and instrumentation.

4. An anabolic chamber as recited in claim 1, wherein the body is fabricated from resin.

5. An anabolic chamber as recited in claim 4, wherein the resin includes an additive.

6. An anabolic chamber as recited in claim 5, wherein the additive is selected from the group consisting of a fungicide, a flame-retardant, an anti-static agent, an anti-microbial agent and an improved heat transfer component.

7. An anabolic chamber as recited in claim 1, further comprising a sensor operatively connected to the control module for determining a temperature of the interior and a heating element attached to the body and activated by the control module based upon the temperature of the interior.

8. An anabolic chamber as recited in claim 7, wherein the heating element is removably coupled to the anabolic chamber.

9. An anabolic chamber as recited in claim 1, wherein the walls of the body are double-walled and define a space therebetween for receiving a fluid.

10. An anabolic chamber as recited in claim 9, further comprising support ribs disposed within the space between the walls to strengthen the body.

11. An anabolic chamber as recited in claim 10, wherein at least one of the ribs defines a throughbore continuously between the walls for providing access to the interior.

12. An anabolic chamber as recited in claim 11, wherein the throughbore is 1.5 inches in diameter.

13. An anabolic chamber as recited in claim 9, further comprising a plurality of shelves within the interior, each shelf defining a hollow in fluid communication with the space.

14. An anabolic chamber as recited in claim 1, wherein the portion is a solid portion in a bottom of the body capable of being drilled out for creating a threaded drain hole.

15. An anabolic chamber having an interior for storing specimens and a control system for maintaining desired environmental conditions within the interior, comprising:
    a box-shaped body portion including inner and outer walls, a fluid jacket space defined between at least three inner walls and the outer walls, the jacket space at least partially surrounding the interior of the anabolic chamber; and
    at least one rib extending between the inner and outer walls and through the jacket space for increasing a structural integrity of at least one of the three inner and outer walls and for providing at least one location to allow drilling out a throughbore through the at least one rib, such that the throughbore extends continuously from the interior of the chamber to an exterior of the chamber.

16. A method for creating an anabolic chamber for storing in vitro fertilization embryos comprising the steps of:
    forming a chamber having an inner wall, an outer wall and a plurality of support ribs between the inner and outer walls, the chamber defining an opening;
    modifying at least one of the plurality of the support ribs to provide access to an interior of the chamber;
    providing a door to selectively seal the opening; and
    applying a heating element to the double-walled chamber for controlling a temperature of the interior of the chamber.

17. A method as recited in claim 16, further comprising the step of filling an inner space between the outer and inner walls with treated water.

18. A method as recited in claim 16, wherein the step of forming is by rotational molding.

19. A method as recited in claim 16, wherein the chamber is fabricated from resin.

20. A method as recited in claim 19, wherein the resin is selected from the group consisting of polyurethane, polycarbonate, polyethylene, polytetrafluoroethylene and polycarbonite.

21. A method as recited in claim 19, wherein the resin is treated with an additive.

22. An incubator defining an interior and comprising:
    a jacket surrounding the interior of the incubator and defining a jacket space for receiving fluid therein such that the fluid is sealed from the interior; and
    a shelf depending from the incubator into the interior and defining an inner sealed hollow in fluid communication with the jacket space.

23. An incubator as recited in claim 22, wherein the shelf is integrally formed with the incubator.

24. A method for creating a chamber for cell culturing comprising the steps of:
    forming a chamber having an inner wall, an outer wall and at least one support rib between the inner and outer walls, the chamber defining an opening;
    modifying the at least one support rib to provide access to an interior of the chamber;
    providing a door to selectively seal the opening; and
    applying a heating element to the double-walled chamber for controlling a temperature of the interior of the chamber.

* * * * *